US007886738B2

(12) United States Patent
Walker

(10) Patent No.: US 7,886,738 B2

(45) Date of Patent: Feb. 15, 2011

(54) APPARATUS FOR DELIVERY OF AN AEROSOLIZED MEDICATION TO AN INFANT

(76) Inventor: Kelly Walker, 310 N. Villa Ave., Villa Park, IL (US) 60181

( * ) Notice: Subject to any disclaimer, the term of this patent is extended or adjusted under 35 U.S.C. 154(b) by 667 days.

(21) Appl. No.: 10/975,754

(22) Filed: Oct. 28, 2004

(65) Prior Publication Data

US 2006/0090751 A1 May 4, 2006

(51) Int. Cl.
*A61M 11/00* (2006.01)
*A61M 15/00* (2006.01)
*A61M 16/00* (2006.01)

(52) U.S. Cl. ............................ 128/200.14; 128/200.24; 128/203.12; 128/203.15

(58) Field of Classification Search ............ 128/200.14, 128/200.21, 200.11, 200.24, 203.28, 204.18, 128/200.22, 203.12; 446/89, 91, 183, 200, 446/219, 267, 270

See application file for complete search history.

(56) References Cited

U.S. PATENT DOCUMENTS 4,522,604 A * 6/1985 Stubbmann ................. 446/219
4,606,328 A * 8/1986 Thoman ...................... 600/27
4,809,692 A 3/1989 Nowacki et al.
4,832,015 A 5/1989 Nowacki et al.
5,230,648 A * 7/1993 Kelley et al. .................. 446/74
5,357,945 A * 10/1994 Messina ................ 128/200.14
5,690,096 A * 11/1997 Burch ................... 128/204.18
5,704,344 A * 1/1998 Cole ..................... 128/200.14
5,774,861 A * 6/1998 Spector ...................... 704/275
5,803,063 A * 9/1998 Corey .................... 128/203.12
5,853,002 A * 12/1998 Kawasaki ............. 128/200.14
D428,140 S * 7/2000 Swan ........................ D24/112
6,238,263 B1 * 5/2001 Bennett ...................... 446/330
6,253,058 B1 * 6/2001 Murasaki et al. ............ 434/308
6,315,163 B1 * 11/2001 Shu ............................ 222/39
6,588,420 B1 * 7/2003 Burch .................. 128/200.24
6,626,168 B1 9/2003 Carroll et al.
6,652,382 B1 * 11/2003 Karussi et al. ................ 463/30
6,718,969 B1 * 4/2004 Rubin et al. ........... 128/200.14
6,748,949 B2 6/2004 Smaldone
6,857,427 B2 * 2/2005 Ziegler et al. .......... 128/200.23
6,997,772 B2 * 2/2006 Fong .......................... 446/175
D548,331 S * 8/2007 Tseng ....................... D24/110
2003/0013376 A1 * 1/2003 Larson et al. ............... 446/236
2005/0194005 A1 * 9/2005 Berube et al. .......... 128/200.14
2006/0160458 A1 * 7/2006 Peach .......................... 446/72

* cited by examiner

*Primary Examiner*—Steven O Douglas
*Assistant Examiner*—Annette F Dixon
(74) *Attorney, Agent, or Firm*—Wood, Phillips, Katz, Clark & Mortimer

(57) ABSTRACT

Disclosed is an apparatus for delivering an aerosolized medication to an infant. The apparatus includes a plaything having a fanciful image. A bore passageway extends through the plaything. The fanciful image has features attractive to an infant where one of the features includes an opening to a first end of the bore passageway. A second end of the bore passageway is adapted to be attached to a nebulizing assembly. The nebulizing assembly is adapted to deliver inhalable aerosolized medication into the bore passageway to facilitate inhalation of the medication by the infant when the opening is proximate to the nose and mouth region of the infant.

10 Claims, 2 Drawing Sheets

APPARATUS FOR DELIVERY OF AN AEROSOLIZED MEDICATION TO AN INFANT

BACKGROUND

This disclosure relates to an apparatus for delivery of an aerosolized medication, and more particularly to an apparatus for delivery of an aerosolized medication to infants and small children.

Nebulization is the application of a medication to a patient by means of an mist, or aerosol, inhaled into the lungs of a patient. There are a number of methods for producing the mist from the medication and therefore there are a number of delivery systems. For example, the medication may be packaged with a dilutent in a small pressurized canister or cartridge which interfits with a mouth piece. The patient places the mouthpiece in his or her mouth and depresses the cartridge, thereby releasing a measured amount of the aerosolized medication which is inhaled through the mouthpiece. Although effective for use by most adults, such a cartridge delivery system is not suitable for infants and small children.

As a result, a face mask is one option that may be used to deliver aerosolized drugs into the lungs of infants and small children who may be suffering from asthma or the like. The face mask, typically positioned on or in the vicinity of the nose and mouth of the child, is attached to a nebulizer assembly via a short flexible tube (e.g., a seven inch accordion plastic tube). The nebulizer assembly is then coupled to a nebulizer air compressor via a segment of plastic tubing.

A nebulizer treatment typically begins when a pre-measured amount of liquid medication (e.g., albuterol) is placed in a nebulizer reservoir of the nebulizer assembly. Upon application of power to the nebulizer air compressor, pressurized air delivered via an aperture proximate to the reservoir causes the liquid medication to be converted into a fine mist. The mist is then inhaled by the child for 15 to 20 minutes.

Unfortunately, infants and small children do not like the "taste" of the mist, the sound generated by operation of the nebulizer air compressor, and the physical restriction of the face mask. As a result, they may cry and/or turn away from the mask, causing much of the mist to be released, unused, into the environment rather than into their lungs.

Many prior art pediatric inhaler/nebulizer designs have addressed one or more of these problems. For example, U.S. Pat. No. 4,832,015 discloses a mask with a bubble design that flexes inwardly to give an indication that the infant is inhaling the mist. Such a bubble design however, does not alleviate the discomfort and/or fear experienced by the infant. Similarly, U.S. Pat. No. 4,809,692 discloses a mask that includes a whistle to provide an audible signal that the infant is breathing in the mist properly. Again, such a design does not alleviate the discomfort and/or fear experienced by the infant. Another mask assembly is disclosed in U.S. Pat. No. 6,626,168. The mask assembly includes a nipple coupled to the mask to encourage the infant to hold the mask. Although alleviating some of the discomfort associated with the mask abutting the infants face, the mask with the nipple may not be enough of a distraction to span the 15 to 20 minute time frame required for delivery of the medication.

SUMMARY

Disclosed is an apparatus for delivering an aerosolized medication to an infant. The apparatus includes a plaything having a fanciful image with a bore passageway extending through the plaything. The fanciful image has features attractive to an infant where one of the features includes an opening to a first end of the bore passageway. A second end of the bore passageway is adapted to be attached to a nebulizing assembly. When actuated by a nebulizing air compressor, the nebulizing assembly delivers inhalable aerosolized medication into the bore passageway to facilitate inhalation of the medication by the infant when the opening is proximate to the nose and mouth region of the infant. The infant is attracted to the fanciful image, and faces the image and thus the first end of the bore passageway. The mouth and nose of the infant remains directed toward the bore passageway, and the infant inhales a maximum amount of the aerosolized medication.

In another embodiment the apparatus for delivering an aerosolized medication to an infant includes a length of tubing having a first end and a second end, and a plaything. The plaything is removably attached to a portion of the length of tubing proximate to the first end. The plaything includes a fanciful image and has a bore passageway extending therethrough, sized to be received by the length of tubing. The fanciful image has features attractive to an infant where one of the features includes an opening. A first end of the bore passageway communicates with the opening in the plaything. The second end of the length of tubing is adapted to be attached to a nebulizing assembly. The nebulizing assembly is configured to deliver inhalable aerosolized medication into the length of tubing and the bore passageway to facilitate inhalation of the aerosolized medication by an infant when the first end of the length of tubing is proximate the nose and mouth region of the infant, and the infant is attracted to and facing the plaything.

In yet another embodiment, the apparatus for delivering an aerosolized medication to an infant includes a length of tubing having a first end and a second end, and a plaything removably attached to the length of tubing proximate to the first end. The plaything includes a fanciful image attractive to an infant. The second end of the length of tubing is adapted to be attached to a nebulizing assembly where the nebulizing assembly is adapted to deliver inhalable aerosolized medication into the length of tubing to facilitate inhalation of the medication by an infant when the first end is proximate to the nose and mouth region of the infant, and the infant is attracted to and facing the plaything.

Other objects, advantages and novel features of the present disclosure will become apparent from the following detailed description when considered in conjunction with the accompanying drawings.

DETAILED DESCRIPTION

Figure 2:
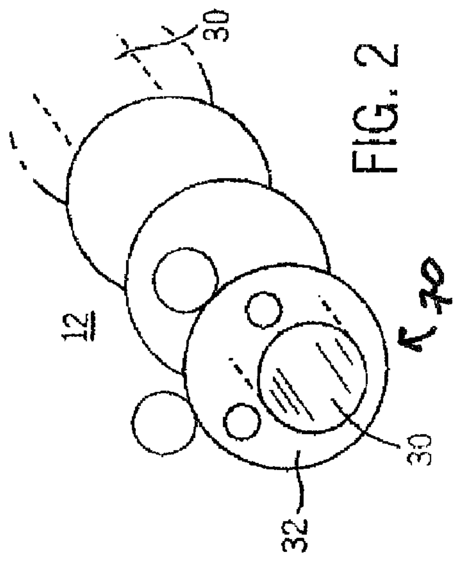
FIG. 2 is a more detailed perspective view of the plaything of the apparatus for delivering an aerosolized medication of FIG. 1.

While the present disclosure may be susceptible to embodiment in different forms, there is shown in the drawings, and will be described herein in detail, one or more embodiments with the understanding that the present description is to be considered an exemplification of the principles of the disclosure and is not intended to be exhaustive or to limit the disclosure to the details of construction and the arrangements of components set forth in the following description or illustrated in the drawings.

Figure 1:
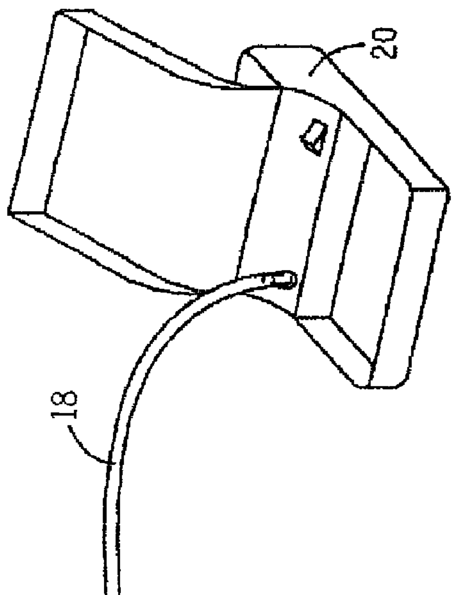
FIG. 1 is a perspective/schematic view of a nebulizing system including an apparatus for delivering an aerosolized medication to an infant according to an embodiment of the invention.
Figure 1:
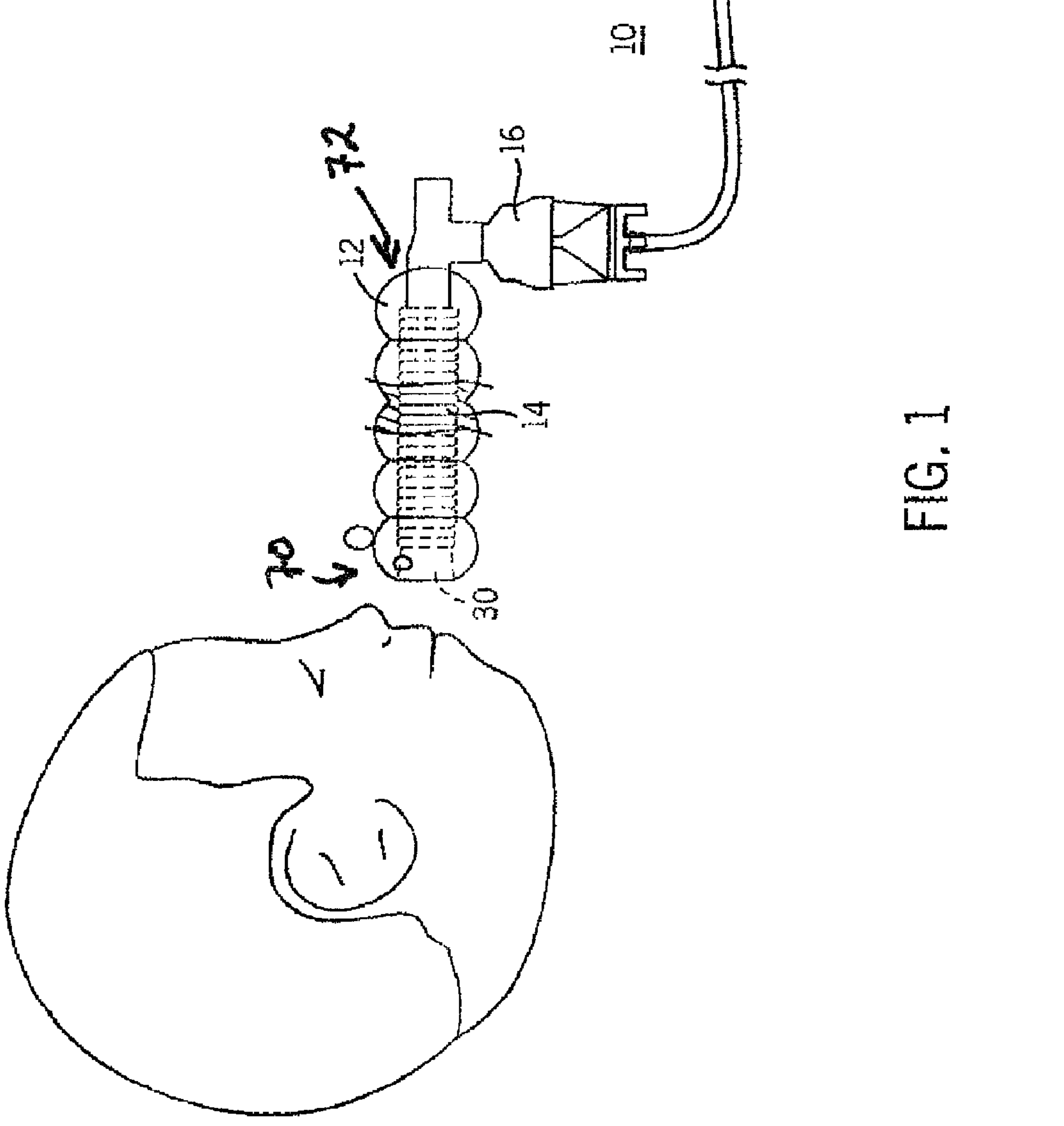

FIG. 1 is a perspective view of a nebulizing system 10 according to an embodiment of the invention. The nebulizing system 10 includes a plaything 12, an optional length of flexible tubing 14, a nebulizer assembly 16, plastic tubing 18 and a nebulizer air compressor 20. As illustrated in FIG. 1, the plaything 12 is coupled to the nebulizer assembly 16 via the flexible tubing 14. It is contemplated however, that the plaything 12 may be directly coupled to the nebulizer assembly 16 as discussed in connection with FIG. 2.

The nebulizing assembly 16 is coupled to the nebulizer air compressor 20 via the plastic tubing 18. The nebulizing assembly 16 may be any well-known nebulizing assembly configured to receive a liquid medication and in response to operation of the nebulizer air compressor 20, deliver suitable inhalable aerosolized medication.

For example, a typical nebulizer assembly 16 may include a chamber defined by a top and bottom dome-like portion where the top portion includes a nebulizer reservoir for receiving the liquid medication and where the bottom portion includes a tiny aperture in communication with the nebulizer air compressor 20 via the plastic tubing 18. During operation, the configuration of the top and bottom portions in conjunction with delivery of pressurized air to the nebulizer reservoir causes the liquid medication to become aerosolized.

FIG. 2 is a more detailed perspective view of the plaything 12 coupled to nebulizing assembly 16. The plaything 12 includes a bore passageway 30 extending therethrough and has a first open end 70 and a second open end 72. The plaything 12 also includes a fanciful image 32 having features attractive to an infant. One of the features includes an opening communicating with bore passageway 30. In the illustrated example, a face having facial features such as eyes, a nose and a mouth with the opening represent a portion of the fanciful image 32. Although illustrated using the animated face, the fanciful image could be one of any number of suitable fanciful images appealing or attractive to an infant or child. For example, the fanciful image may be an insect (e.g., a friendly looking caterpillar), an animal (e.g., a teddy bear), a doll, a black and white pattern, a color pattern, or the like. Similarly, the first bore opening may be incorporated into the features of the fanciful image in one of any number of ways.

The plaything 12 may also include any number of enhancements that make it more attractive to an infant or small child so that the child is attracted to and faces the plaything 12 as aerosol medication is administered through bore passageway 30. For example, the plaything 12 may include an audible sound generator to generate music or other appealing sounds. Similarly, the plaything 12 may include a noise generating rattle, for example, including loose elements safely inside the ears and/or nose of the plaything. The plaything 12 may also include a light generating means such as one or more white or colored light emitting diodes (LED), an organic LED, to name a few. Further, the plaything 12 may include a child-safe reflecting means or a "sparkly" means via the use of, for example, glitter, metallic threads or a mirror.

As previously mentioned, a first open end of the bore passageway 30 is in communication with the opening incorporated into the fanciful image 32, while the second open end of the bore passageway 30 is coupled to the nebulizing assembly. The second open end may be coupled to the nebulizing assembly using a direct or indirect mating means. Thus, the second open end may be configured in one of any number of suitable ways to receive inhalable aerosolized medication delivered from the mated nebulizing assembly 16. For example the interior of the second open end may be threaded and sized to directly receive the nebulizing assembly 16. Alternatively, both the second open end of the plaything 12 and a portion of the nebulizing assembly 16 may be configured to receive a snug-fitting mating tube inserted therebetween.

When mated to the plaything 12, the nebulizing assembly 16 delivers aerosolized medication to the bore passageway 30. Delivery of the aerosolized medication to the bore passageway 30 facilitates inhalation of the aerosolized medication by the infant when the opening, in communication with the first open end of the bore passageway 30, is proximate to the nose and mouth region of the infant.

As mentioned in connection with FIG. 1, the plaything 12 may be coupled to the nebulizer assembly 16 via the flexible tubing 14 and the bore passageway 30. In such a configuration, the flexible tubing 14 is removably disposed in the bore passageway 30 of the plaything 12 where a first end of the flexible tubing 14 terminates in the first open end thereby enabling the bore passageway 30 to communicate with the opening (e.g., the mouth 34 of the fanciful image 32). Thus, a portion of the flexible tubing 14 is encased within the plaything 12 via the use of the bore passageway 30 with the plaything 12 preferably proximate to the first end of the flexible tubing 14 to enable easy viewing by the infant.

A second end of the flexible tubing 14 is configured to mate with the nebulizing assembly 16. Thus, when mated to the plaything 12, the nebulizing assembly 16 delivers aerosolized medication to the flexible tubing 14. Delivery of the aerosolized medication into the flexible tubing 14 facilitates inhalation of the aerosolized medication by the infant when the opening is proximate to the nose and mouth region of the infant, and the infant faces the plaything 12.

Figure 3:
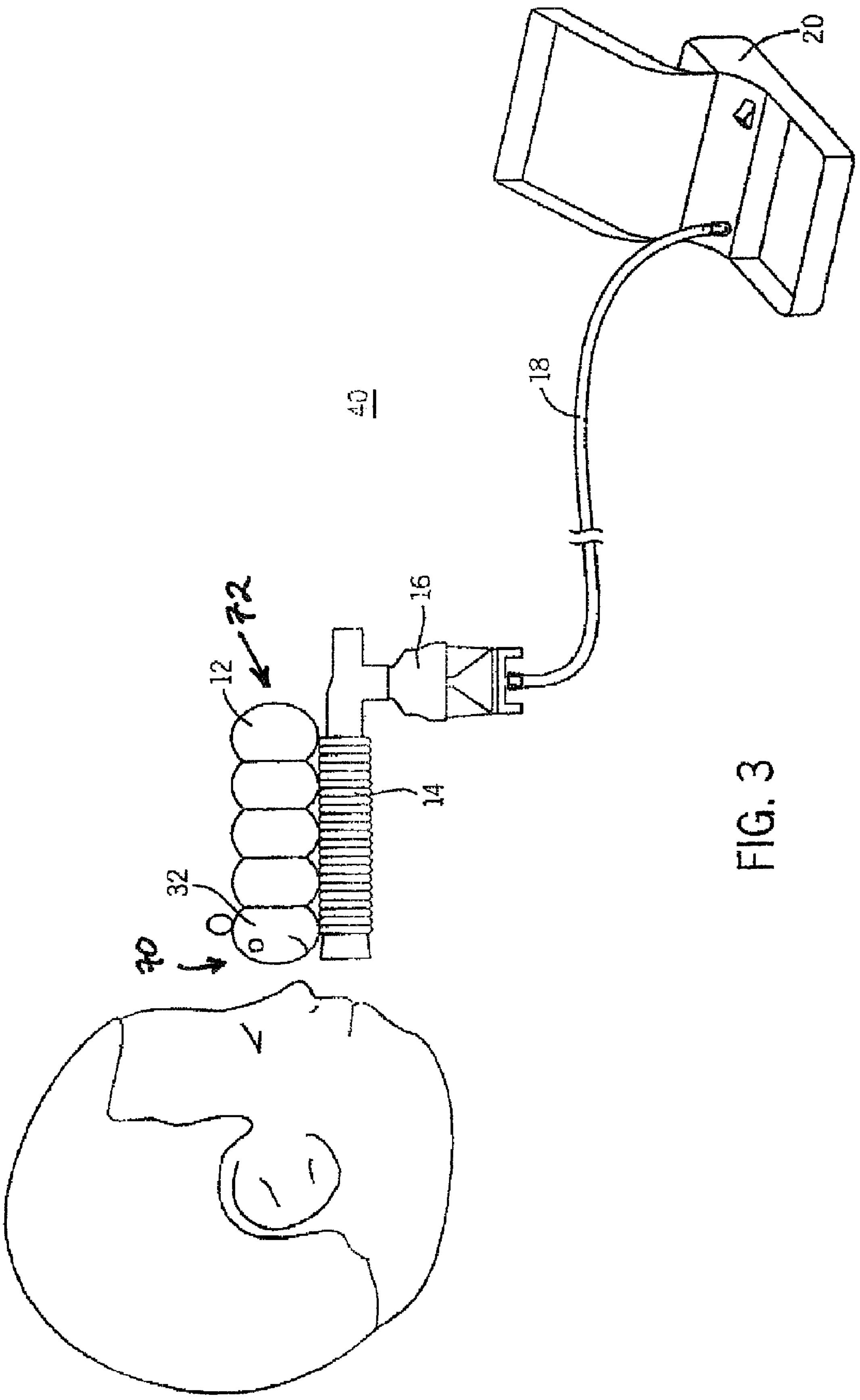
FIG. 3 is a perspective/schematic view of another apparatus for delivering an aerosolized medication to the infant.

FIG. 3 is a perspective/schematic view of another apparatus for delivering an aerosolized medication to the infant. As mentioned in connection with FIG. 1, the plaything 12 may be attached to the flexible tubing 14 where the flexible tubing 14 has a first open end and a second open end. The plaything 12 is removably attached to the flexible tubing 14, preferably proximate to the first open end. The plaything 12 includes the fanciful image 32 attractive to an infant. In this embodiment however, the fanciful image does not incorporate the opening. Instead, the first open end provides an exit point for the aerosolized medication. The second open end is adapted to be attached to a nebulizing assembly where the nebulizing assembly delivers inhalable aerosolized medication into the flexible tubing 14 to facilitate inhalation of the medication by an infant when the first open end is proximate to the nose and mouth region of the infant, and the infant is facing plaything 12.

While embodiments have been illustrated and described in the drawings and foregoing description, such illustrations and descriptions are considered to be exemplary and not restrictive in character, it being understood that only illustrative embodiments have been shown and described and that all changes and modifications that come within the spirit of the invention are desired to be protected. The applicant has provided description and figures which are intended as illustrations of embodiments of the disclosure, and are not intended to be construed as containing or implying limitation of the disclosure to those embodiments.

The invention claimed is:

1. An apparatus adapted to be coupled to a nebulizing assembly having a reservoir for liquid medication and incorporating a tube having a first end for receiving medication from the reservoir and an exit end used for delivering an aerosolized medication to an infant, the tube having no other exits, the apparatus comprising:

a plaything adapted to be coupled to the tube of the nebulizing assembly and having a first end and a spaced apart second end, the plaything including a fanciful image with friendly features;

a first opening formed in the first end of the plaything that forms part of the fanciful image;

a second opening formed in the second end of the plaything and adapted to be coupled to the tube of the nebulizing assembly;

a bore passageway extending through the plaything and, the bore passageway being co-linear with a bore passageway of the tube of the nebulizing assembly when the plaything is coupled to the tube; and wherein the nebulizing assembly is adapted to deliver inhalable aerosolized medication through the bore passageway of the plaything to the first opening to facilitate inhalation of the medication by the infant when the first opening is proximate to the nose and mouth region of the infant; and wherein the first opening in the plaything is no smaller than the exit end of the tube.

2. The apparatus of claim 1, wherein the fanciful image comprises an animated insect.

3. The apparatus of claim 1, wherein the fanciful image comprises an animated animal.

4. The apparatus of claim 1, wherein the fanciful image comprises a doll.

5. The apparatus of claim 1, wherein the fanciful image comprises facial features and wherein the first opening comprises a mouth of the facial features.

6. An apparatus adapted to be coupled to a nebulizing assembly that includes a tube having an exit end and a first end for receiving medication, the tube used for delivering an aerosolized medication to an infant, the tube having no other exits, the apparatus comprising:

a plaything adapted to be coupled to the tube of the nebulizing assembly and having a first end and a spaced apart second end, the plaything including a fanciful image with the friendly features to create a pleasant image for an infant to look at;

a first opening formed in the first end of the plaything that forms the mouth of the fanciful image;

a second opening formed in the second end of the plaything that is adapted to be coupled to the tube of the nebulizing assembly;

a bore passageway extending through the plaything and adapted to fluidly couple the first opening to the second opening so that aerosolized medication can exit the first opening, the bore passageway arranged to be co-axial with a bore passageway of the tube of the nebulizing assembly when the plaything is coupled to the tube, the plaything covering the tube so that the tube exit end is not exposed to the infant;

wherein the nebulizing assembly is adapted to deliver inhalable aerosolized medication through the bore passageway of the tubing through the plaything to the first opening to facilitate inhalation of the medication by the infant when the first opening is proximate to the nose and mouth region of the infant; and wherein the first opening is no smaller in diameter than the tube of the nebulizing assembly.

7. The apparatus of claim 6, wherein the fanciful image comprises an animated insect.

8. The apparatus of claim 6, wherein the fanciful image comprises an animated animal.

9. The apparatus of claim 6, wherein the fanciful image comprises a doll.

10. The apparatus of claim 6, wherein the fanciful image comprises facial features and wherein the first opening comprises a mouth of the facial features.

* * * * *